United States Patent
Cheng

(10) Patent No.: US 10,539,528 B2
(45) Date of Patent: Jan. 21, 2020

(54) STACKED NANOFLUIDICS STRUCTURE

(71) Applicant: INTERNATIONAL BUSINESS MACHINES CORPORATION, Armonk, NY (US)

(72) Inventor: Kangguo Cheng, Schenectady, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 15/847,334

(22) Filed: Dec. 19, 2017

(65) Prior Publication Data

US 2019/0187092 A1   Jun. 20, 2019

(51) Int. Cl.
| | | |
|---|---|---|
| H01L 21/02 | (2006.01) | |
| G01N 27/414 | (2006.01) | |
| H01L 21/306 | (2006.01) | |
| H01L 29/06 | (2006.01) | |
| B01L 3/00 | (2006.01) | |
| H01L 29/16 | (2006.01) | |

(52) U.S. Cl.
CPC .... *G01N 27/4146* (2013.01); *B01L 3/502707* (2013.01); *B01L 3/502715* (2013.01); *H01L 21/02532* (2013.01); *H01L 21/02603* (2013.01); *H01L 21/30604* (2013.01); *H01L 29/0673* (2013.01); *H01L 29/16* (2013.01); *B01L 2300/0896* (2013.01); *B01L 2300/16* (2013.01)

(58) Field of Classification Search
CPC ......... B01L 3/502707; B01L 3/502715; B01L 2300/0896; B01L 2300/16; G01N 27/4146
See application file for complete search history.

(56) References Cited

U.S. PATENT DOCUMENTS

| 8,080,152 B2 | 12/2011 | Sirringhaus |
| 8,158,409 B2 | 4/2012 | Wei et al. |
| 8,778,768 B1 | 7/2014 | Chang et al. |
| 9,224,673 B2 | 12/2015 | Chen et al. |
| 9,287,357 B2 | 3/2016 | Rodder et al. |
| 9,450,043 B2 | 9/2016 | Nuzzo et al. |
| 10,134,901 B1 * | 11/2018 | Pawlak ................ H01L 29/785 |
| 10,261,065 B2 | 4/2019 | Ramsey et al. |

(Continued)

FOREIGN PATENT DOCUMENTS

KR   101641085 B1   7/2016

OTHER PUBLICATIONS

Jeon, "Optically Fabricated Three Dimensional Nanofluidic Mixers for Microfluidic Devices", Nano Letters 2005 vol. 5, No. 7; Jul. 2005; pp. 1351-1356.

*Primary Examiner* — Didarul A Mazumder
*Assistant Examiner* — Wasiul Haider
(74) *Attorney, Agent, or Firm* — Tutunjian & Bitetto, P.C.; Vazken Alexanian

(57) ABSTRACT

Methods and devices for a stacked nanofluidic sensor are described. The stacked nanofluidic sensor and methods for forming a nanosheet stack of at least two alternating layers of a first nanosheet material and a second nanosheet material on a substrate. Additionally, a gate structure is formed on the nanosheet stack. Further, nanofluidic channels are formed within the gate structure, including removing each layer of the first nanosheet material within the gate structure to form a channel configured to receive a nanofluidic sample.

16 Claims, 18 Drawing Sheets

(56) References Cited

U.S. PATENT DOCUMENTS

| | | |
|---|---|---|
| 2007/0122313 A1 | 5/2007 | Li et al. |
| 2011/0311722 A1 | 12/2011 | Faris |
| 2015/0068901 A1 | 3/2015 | Mannion et al. |
| 2015/0295084 A1 | 10/2015 | Obradovic et al. |
| 2016/0074828 A1* | 3/2016 | Chen .................... B01J 19/0046 506/37 |
| 2016/0184821 A1 | 6/2016 | Hobbs et al. |
| 2016/0187288 A1* | 6/2016 | Cheng ................ G01N 27/4145 205/775 |
| 2016/0228846 A1 | 8/2016 | Chen et al. |
| 2018/0301531 A1* | 10/2018 | Xie .................... H01L 29/0673 |

* cited by examiner

STACKED NANOFLUIDICS STRUCTURE

BACKGROUND

Technical Field

The present invention generally relates to nanofluidics, and more particularly to nanofluidic sensors formed with nanosheets.

Description of the Related Art

Nanofluidics is a technology that is useful for analyzing fluids in nanometer scale channels. By using flow channels sized on the order of nanometers, various fluid properties can be better evaluated than at larger scales. For example, biosensing and screening can be more accurately performed with nanofluidic structures.

However, the geometric dimensions of the nanofluidic structure effects the accuracy of measurements. For example, when passing an electrical signal through a sample, the distance through the sample that the signal must pass will affect how greatly the signal is changed. Accordingly, imprecision in forming channels that carry a fluid sample introduces error into measurements of a signal passed therethrough.

SUMMARY

In accordance with an embodiment of the present invention, a method is described for forming a stacked nanofluidic sensor. The method includes forming a nanosheet stack of at least two alternating layers of a first nanosheet material and a second nanosheet material on a substrate. Additionally, the method includes forming a gate structure on the nanosheet stack. The method further includes forming nanofluidic channels within the gate structure, including removing each layer of the first nanosheet material within the gate structure to form a channel configured to receive a nanofluidic sample.

In accordance with an embodiment of the present invention, a method is described for forming a stacked nanofluidic sensor device. The method includes forming concurrently forming nanosheet stacks of at least two alternating layers of a first nanosheet material and a second nanosheet material in each of at least a first region and a second region on a substrate. Additionally, the method includes concurrently forming a dummy gate over and around the nanosheet stack in each of the first region and the second region. The method further includes concurrently forming gate structures in each of the first region and the second region by a gate replacement process, including replacing each layer of the first material in each of the first and the second region with a gate conductor. A step is included for forming a transistor in the first region including the gate structure in the first region, as well as forming a nanofluidic sensor in the second region by removing a gate conductor from within the gate structure in the second to form channels within the gate structure configured to receive a nanofluidic sample.

In accordance with an embodiment of the present invention, a stacked nanofluidic sensor is described. The stacked nanofluidic sensor includes a gate structure defined by gate spacers, including alternating nanosheet layers therein, wherein at least one of the layers is removed to form at least one nanofluidic channel, and a gate conductor formed within the gate structure, including a fluid sample within the nanofluidic channel.

These and other features and advantages will become apparent from the following detailed description of illustrative embodiments thereof, which is to be read in connection with the accompanying drawings.

BRIEF DESCRIPTION OF THE DRAWINGS

The following description will provide details of preferred embodiments with reference to the following figures wherein.

DETAILED DESCRIPTION

Figure 1:
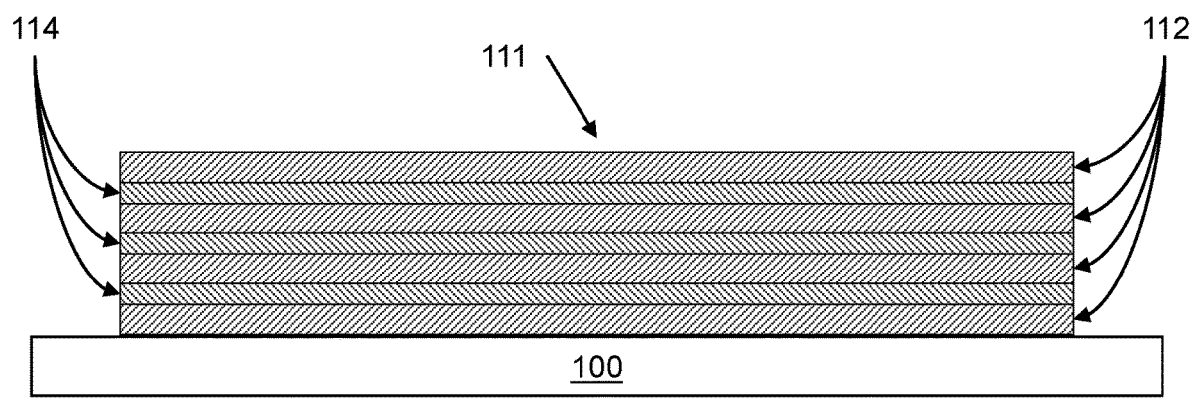
FIG. 1 is a cross-sectional view showing semiconductor layers formed on a substrate of a semiconductor device, in accordance with an embodiment of the present invention.

Described below are aspects of inventive devices having nanofluidic structures, and methods for making such devices.

Nanosheet transistors are a type of transistor that are formed using stacks of two different materials, each material being formed in sheets of nanoscale height. The height of each nanosheet can be precisely controlled in the deposition process. In forming the nanosheet transistor from the stacks, one of the materials can be a sacrificial material. Therefore, upon forming gate structures with the stacks, the sacrificial material may be removed and replaced with a gate metal. As a result, a transistor is formed having a stacked internal structure that alternates between gate metal and a nanosheet material. The width and length of the gate structures can be precisely controlled in the gate formation process.

By using a nanosheet transistor fabrication process to form a gate structure, and then removing the gate metal, a series of vertically stacked channels are formed in the gate structure. A fluid sample is then input into those channels and a current is supplied through a source to a drain to create a signal. As a result, changes in the current supplied, the signal senses various properties of the fluid sample. Accordingly, a nanofluidics sensor is created. Because the nanosheet transistor fabrication process was used, the channels of the nanofluidics sensor have dimensions that are similarly precise to the gates of a nanosheet transistor. The precise dimensions of the channels improve the accuracy of a nanofluidics sensor fabricated with such a process.

Additionally, because the nanofluidics sensor is fabricated with a similarly process to nanosheet transistors, both nanofluidic sensors and nanosheet transistors may be formed concurrently on a substrate to quickly and efficiently fabricate a lab-on-a-chip having sensors, microprocessors and memory integrated on a single substrate.

Exemplary applications/uses to which the present invention can be applied include, but are not limited to: biosensing and screening for disease testing, immunoassaying and nucleic acid assaying, and DNA sequencing, though the present invention may be applied to any scenario involving the measurement of substances suspended in a fluid.

It is to be understood that the present invention will be described in terms of a given illustrative architecture; however, other architectures, structures, substrate materials and process features and steps may be varied within the scope of the present invention.

It will also be understood that when an element such as a layer, region or substrate is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

The present embodiments may include a design for an integrated circuit chip, which may be created in a graphical computer programming language, and stored in a computer storage medium (such as a disk, tape, physical hard drive, or virtual hard drive such as in a storage access network). If the designer does not fabricate chips or the photolithographic masks used to fabricate chips, the designer may transmit the resulting design by physical means (e.g., by providing a copy of the storage medium storing the design) or electronically (e.g., through the Internet) to such entities, directly or indirectly. The stored design is then converted into the appropriate format (e.g., GDSII) for the fabrication of photolithographic masks, which typically include multiple copies of the chip design in question that are to be formed on a wafer. The photolithographic masks are utilized to define areas of the wafer (and/or the layers thereon) to be etched or otherwise processed.

Methods as described herein may be used in the fabrication of integrated circuit chips. The resulting integrated circuit chips can be distributed by the fabricator in raw wafer form (that is, as a single wafer that has multiple unpackaged chips), as a bare die, or in a packaged form. In the latter case the chip is mounted in a single chip package (such as a plastic carrier, with leads that are affixed to a motherboard or other higher level carrier) or in a multichip package (such as a ceramic carrier that has either or both surface interconnections or buried interconnections). In any case the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

Referring now to the drawings in which like numerals represent the same or similar elements and initially to FIG. 1, a step in forming a nanosheet stack 111 of a semiconductor device 10 is depicted according to an embodiment of the present invention.

According to aspects of the invention, forming the semiconductor device 10 may include forming a nanosheet stack 111 of alternating layers of semiconducting material on a substrate 100. The substrate 100 may include, e.g. monocrystalline silicon (Si), however other suitable materials may be use (for example, silicon germanium (SiGe), gallium arsenide (GaAs), silicon carbide (SiC), polycrystalline silicon, and other group IV, III-V, II-VI and semiconducting materials). Additionally, the substrate may be a silicon-on-insulator substrate or a bulk substrate including an insulating layer or buried oxide (BOX) layer formed thereon.

Formed on the substrate 100 is a nanosheet stack 111 of alternating materials. The materials may include at least two semiconducting materials with differing etch selectivity. As an example, the nanosheet stack 111 may include a first nanosheet material 112 that is a sacrificial material including SiGe, and a second nanosheet material 114 including Si. The first nanosheet material 112 and the second nanosheet material 114 may be deposited in alternating fashion to form desired number of layered nanosheets (for example, four layers of the first nanosheet material 112 and three layers of the second nanosheet material 114). The first nanosheet material 112 and second nanosheet material 114 may be formed with any suitable deposition process to permit accurate control of the height of each layer, such as physical vapor deposition (PVD), chemical vapor deposition (CVD), electrochemical deposition (ECD), molecular beam epitaxy (MBE) and atomic layer deposition (ALD) among others.

Figure 2:
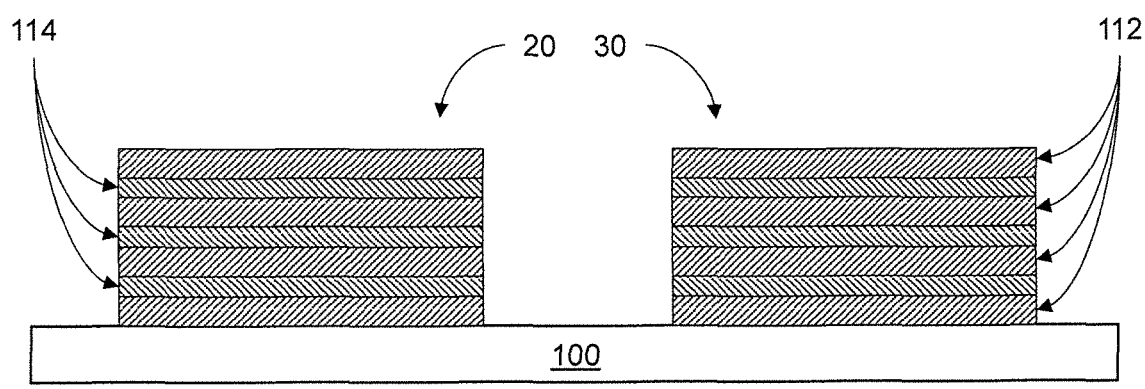
FIG. 2 is a cross-sectional view showing the semiconductor layers of the semiconductor of FIG. 1 patterned into more than one region, in accordance with an embodiment of the present invention.

Referring now to FIG. 2, a step in forming multiple regions on the semiconductor device 10 is depicted according to an embodiment of the present invention.

According to aspects of the invention, a stack of nanosheets, such as the stack 111 described in reference to FIG. 1, may be patterned to form multiple regions on the semiconductor device 10. For example, the nanosheet stack 111 may be patterned into two or more regions, including a first region 20 and a second region 30, however there may be as many regions as desired. The regions may be patterned out of the nanosheet stack 111 using, e.g., an etching process such as a wet etch or dry etch process. Additionally, a lithographic process may be used to pattern the regions, or the regions may be separately deposited as independent nanosheet stacks.

Both the first region 20 and the second region 30 include the same layer structure (i.e. the same nanosheet stack materials with the same number and configuration of layers). The similarity between the two regions permits both first and second regions 20 and 30 to be processed concurrently.

Figure 3:
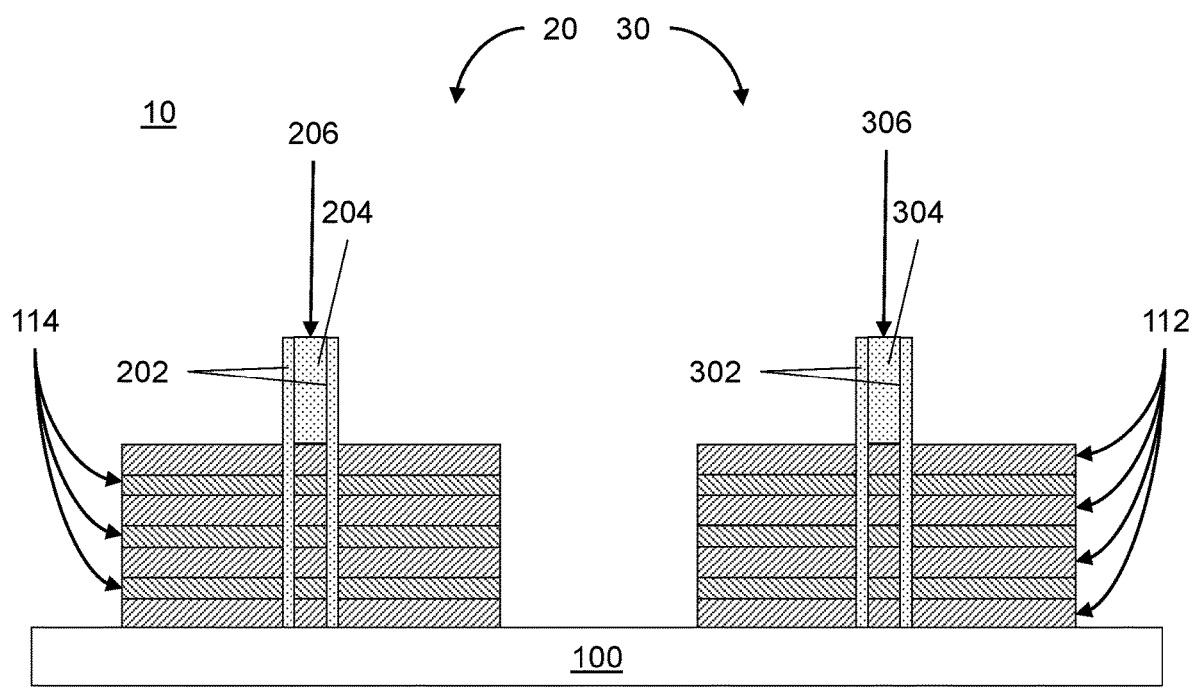
FIG. 3 is a cross-sectional view showing a dummy gate formed in between spacers on each region of the semiconductor device of FIG. 3, in accordance with an embodiment of the present invention.

Referring now to FIG. 3, a step including forming dummy gates 206 and 306 on the semiconductor device 10 is depicted according to an embodiment of the present invention.

According to aspects of the invention, a step for forming a first dummy gate 206 and a second dummy gate 306 on the first region 20 and the second region 30 respectively. Each dummy gate 206 and 306 can include a single or multiple materials. For example, each dummy gate 206 and 306 may include a dummy gate dielectric (e.g., silicon oxide), a dummy gate (e.g., amorphous or polycrystalline silicon), a gate cap (e.g., silicon nitride). Alternatively, According to aspects of the invention, the first dummy gate material 204 is an insulating or a dielectric material, such as, e.g. an oxide or a nitride, that may be deposited by a suitable deposition process, such as those described above, and then patterned, or a mask may be patterned and then the dummy gate material 204 may be deposited.

Similarly, second dummy gate material 304 may be formed of an oxide or nitride material to form a second dummy gate 306. The second dummy gate 306 may be formed concurrently with the first dummy gate 206 to permit faster, more efficient processing the multiple regions on the semiconductor device 10.

First gate spacers 202 and second gate spacers 302 may then be formed on each side of the dummy gates 206 and 306 respectively. The first gate spacers 202 and the second gate spacers 302 may each be formed, e.g., according to a conformal deposition process where a layer of the gate spacer material is conformally deposited over each of the first region 20 and the second region 30. The gate spacer material on horizontal surfaces is then removed, for example, by directional etch (e.g., reactive ion etch (RIE)), to leave only the vertical first gate spacers 202 in the first region 20 and the vertical second gate spacers 302 in the second region 30.

The dummy gates 206 and 306 and their corresponding gate spacers 202 and 302 respectively may be formed over the nanosheet stacks in each of the first region 20 and the second region 30. For example, the first dummy gate 206, as depicted in FIG. 3, extends depth-wise into the page on top of the nanosheet stack of the first region 20, and wrapping around the front and the back of the nanosheet stack down to the substrate 100. The second dummy gate 306 has a similar configuration in the second region 30.

The first dummy gate material 204 may be a different material from the gate spacer material of the first gate spacers 202. As a result, the first dummy gate material 204 may be etched selective to the first gate spacers 202.

Figure 4:
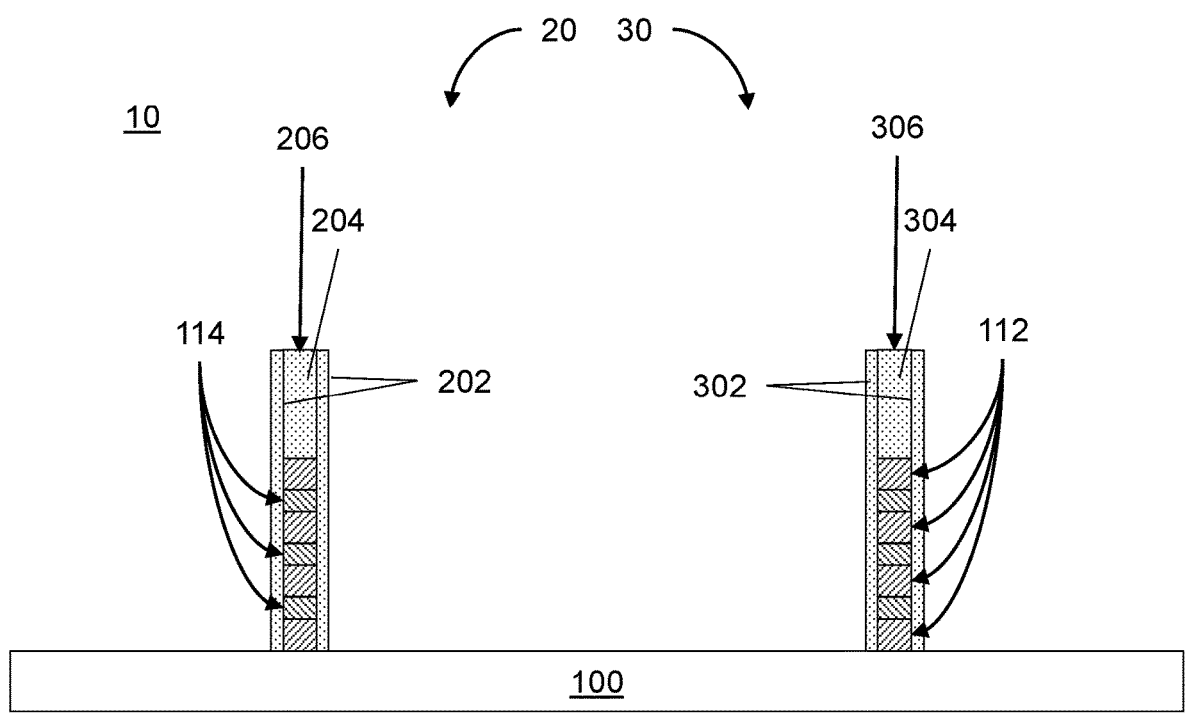
FIG. 4 is a cross-sectional view showing portions of the semiconductor layers removed from the semiconductor device of FIG. 4, in accordance with an embodiment of the present invention.

Referring now to FIG. 4, a step including removing exposed stacks in the first region 20 and the second region 30 on the semiconductor device 10 is depicted according to an embodiment of the present invention.

According to aspects of the invention, there includes a step for removing portions of the nanosheet stacks of the first region 20 and the second region 30. The removed portions of the nanosheet stacks include portions that occupy an area outside of a footprint of the first dummy gate 206 and the second dummy gate 306. As a result, the first dummy gate 206 and the second dummy gate 306 each include a stack of the first nanosheet material 112 and the second nanosheet material 114 that is coextensive in width with the first dummy gate 206 in the first region 20 and with the second dummy gate 306 in the second region 30.

The nanosheet stacks 111 of each region may have the portions removed by, e.g. an etch process, such as those described above, by using the dummy gate 206 and/or 306 and corresponding gate spacer 202 and/or 302 as the mask. In other words, after etching, the nanosheet stack 111 covered by dummy gate 206 and/or 306 and spacer 202 and/or 302 remain and nanosheet stack 111 not covered by dummy gate 206 and/or 306 and spacer 202 and/or 302 is removed. As a result, the first dummy gate 206 may form an etch mask for the nanosheet stack of the first region 20, thus ensuring that the nanosheet stack is patterned to be coextensive with the first dummy gate 206. Similarly, the second dummy gate 306 may form an etch mask for etching portions from the nanosheet stack in the second region 30. The nanosheet stacks of each of the first region 20 and the second region 30 may be patterned concurrently, thus reducing processing steps and processing time.

Figure 5:
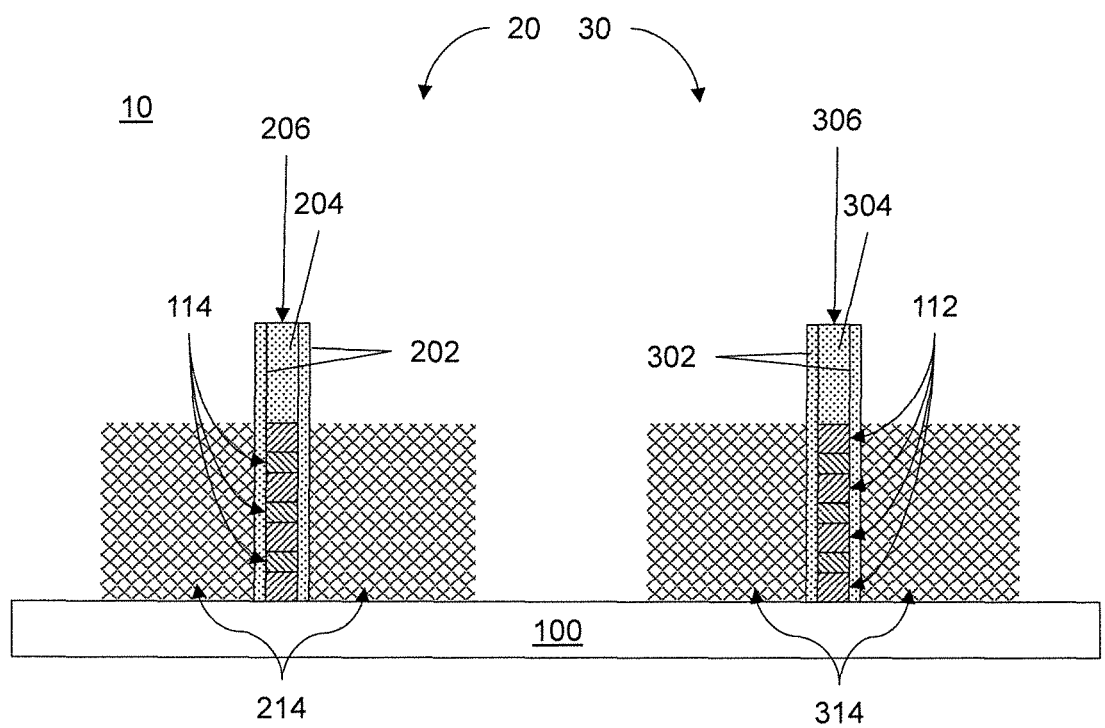
FIG. 5 is a cross-sectional view showing source and drain regions form on the semiconductor device of FIG. 5, in accordance with an embodiment of the present invention.

Referring now to FIG. 5, a step including depositing first source/drain regions 214 and second source/drain regions 314 in the first region 20 and the second region 30 respectively on the semiconductor device 10 is depicted according to an embodiment of the present invention. In some embodiments, inner spacers (not shown) can be formed at the ends of the first nanosheet material 112 (e.g. sacrificial SiGe sheets) before source/drain formation. The inner spacer can be formed by any known technique, for example, by selectively etching a portion of the sacrificial SiGe sheets from ends selective to silicon sheets to create an indent at each end of SiGe sheet. The indent is then filled with a dielectric material to form inner spacer.

According to aspects of the invention, a step includes forming source/drain regions 214 and 314 adjacent to the dummy gates 206 and 306 respectively. The source/drain regions 214 and 314 may occupy an area that is about the same in size and position to the removed portions of the nanosheet stacks. However, the source/drain regions 214 and 314 may also be either larger or smaller than the removed portions of the nanosheet stacks, as long as the source/drain regions 214 and 314 abut the dummy gates 206 and 306 respectively.

The source/drain regions 214 and 314 may be formed from a metal, or other suitable conductor. According to aspects of the invention, the source/drain regions 214 and 314 are formed from silicon by an epitaxially growth process. However, other semiconductor materials may be used to form the source/drain regions 214 and 314. The silicon is grown from the substrate 100 and the gate spacers of the dummy gates 206 and 306. Epitaxially growing the source/drain regions 214 and 314 improves the ability to control the portions of the dummy gate that are left exposed due to greater control of dimensions of the source/drain regions 214 and 314. The source/drain regions 214 and 314 may be grown by an epitaxially process such as, e.g., molecular beam epitaxy (MBE), vapor phase epitaxy, solid phase epitaxy, liquid phase epitaxy, or other suitable growth process.

The epitaxially grown source/drain regions 214 and 314 may include a doped material that is doped, e.g. in situ, or through a separate process from the formation of the source/drain regions 214 and 314. In the latter case, the source/drain regions 214 and 314 may be doped through diffusion or by ion implantation, and may be performed using, e.g., a separate vapor phase epitaxy step.

Figure 6:
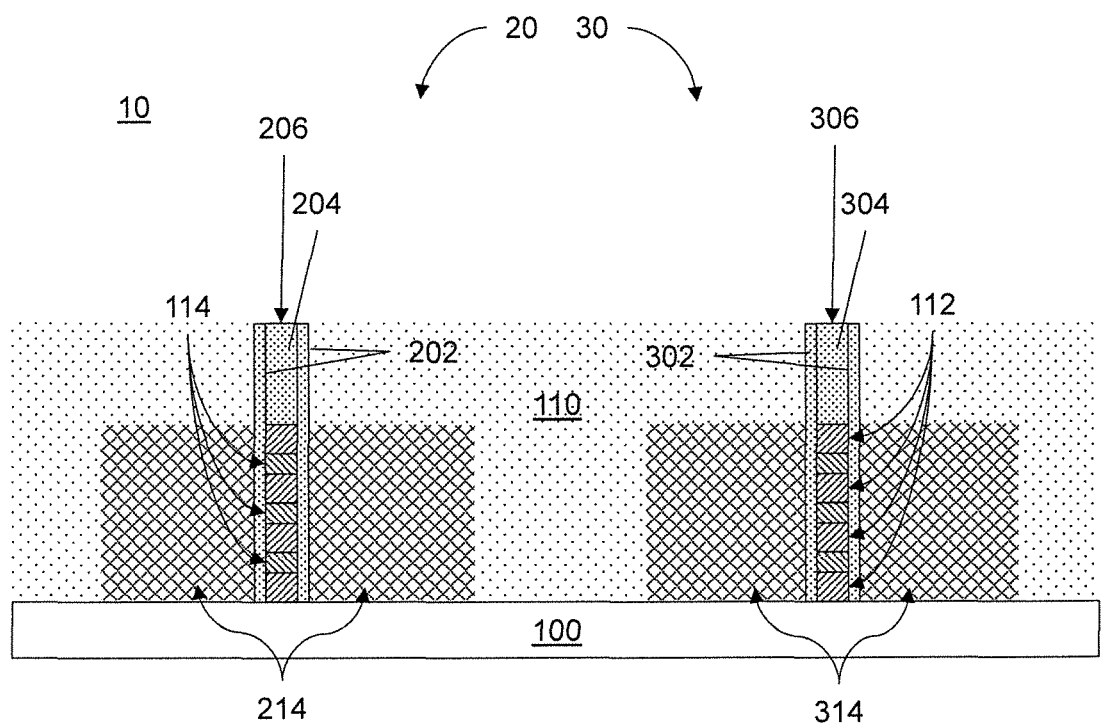
FIG. 6 is a cross-sectional view showing an interlevel dielectric layer formed over the semiconductor device of FIG. 6, in accordance with an embodiment of the present invention.

Referring now to FIG. 6, a step including depositing an interlevel dielectric (ILD) 110 on the semiconductor device 10 is depicted according to an embodiment of the present invention.

According to aspects of the invention, there may be a step for depositing an ILD 110 on the semiconductor device 10. The ILD 110 may be deposited by any suitable deposition process, such as those described above, such that the ILD 110 encompasses components in both the first region 20 and the second region 30 of the semiconductor device 10. By encompassing the components of the semiconductor device 10, the ILD 110 insulates the various components from each other, thus reducing electrical interference between the components, such as a gate of the first region 20 and a gate of the second region 30. To further facilitate the electrical insulation of components, the ILD 110 may be formed, for example, of a, e.g., low-k dielectric material.

To smooth the surface topography of the ILD 110, and to expose the dummy gates 206 and 306, the ILD 110 may be planarized with a planarization process, including, e.g., chemical mechanical planarization (CMP), or any other suitable planarization process. Planarizing the ILD 110 down to the dummy gates 206 and 306 exposes the dummy gates, thus permitting access to the dummy gates 206 and 306 in subsequent processing.

Figure 7:
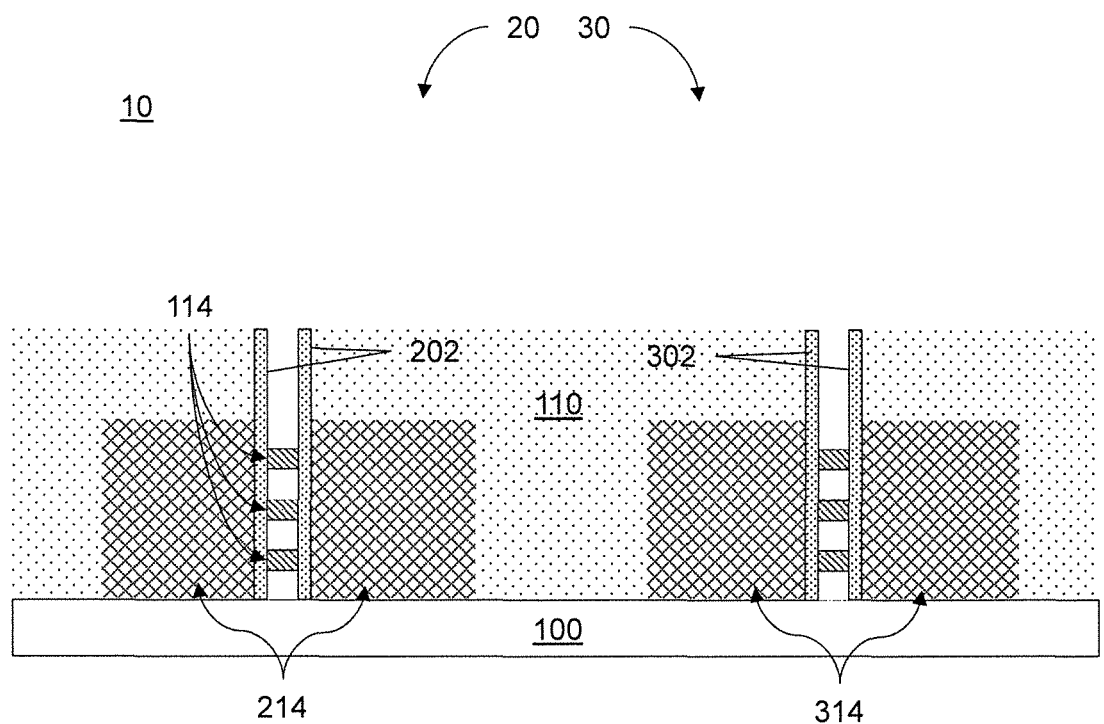
FIG. 7 is a cross-sectional view showing the dummy gates and one of the alternating layers of the stacks removed from the semiconductor device of FIG. 7, in accordance with an embodiment of the present invention.

Referring now to FIG. 7, a step including removing the dummy gates 206 and 306 on the semiconductor device 10 is depicted according to an embodiment of the present invention.

According to aspects of the invention, a step is included for removing the first dummy gate material 204 and the second dummy gate material 304. The first dummy gate material 204 and the second dummy gate material 304 may be removed concurrently through a single etch process. The etch process may be any suitable selective etch process, such as those described above. The etch process may include forming a mask over the semiconductor device 10, patterned to expose the first dummy gate material 204 and the second dummy gate material 304.

However, because the first dummy gate material 204 and the second dummy gate material 304 are different from the materials of the first gate spacers 202 and the second spacer 302, respectively, the first dummy gate material 204 and the second dummy gate material 304 may be etched according to the etch selectivity from the first gate spacers 202 and the second spacer 302. Accordingly, no masking step is required to perform the etching.

In another etch process, the first nanosheet material 112 is removed from the first region 20 and the second region 30. Because the first nanosheet material 112 is a sacrificial material different from the second nanosheet material 114 and from the first and second gate spacers 202 and 302, such as, e.g., SiGe, the first nanosheet material 112 may selectively etchable from those materials. Therefore, the first nanosheet material 112 may be removed by a selective etch process according to the etch selectivity. Accordingly, no masking step is required to perform the etching.

The first dummy gate material 204 and the second dummy gate material 304 may be etched concurrently or separately. Similarly, the first nanosheet material 112 may be etched from the first region 20 and the second region 30 concurrently or separately. Upon removing the first and second dummy gate material 204 and 304 respectively, and the first nanosheet material 112, a hollow gate structure remains with the second nanosheet material 114 extending between the first gate spacers 202 and between the second spacer 302.

Figure 8:
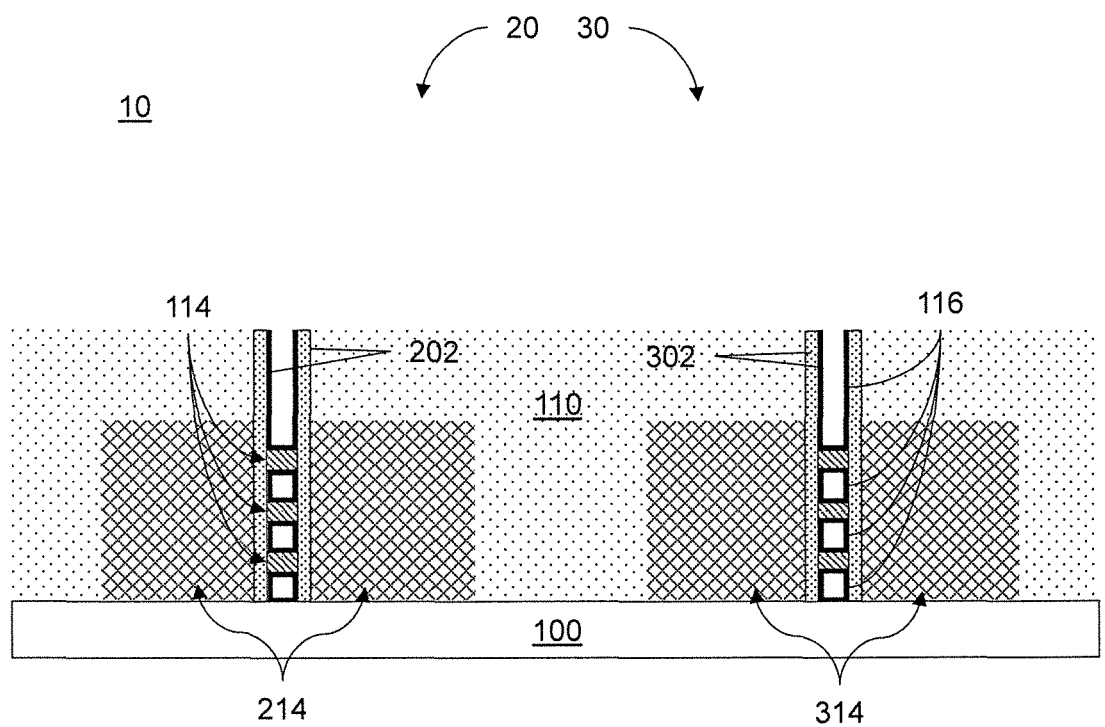
FIG. 8 is a cross-sectional view showing a dielectric layer formed between the spacers and the remaining layer of the alternating layers of the semiconductor device of FIG. 8, in accordance with an embodiment of the present invention.

Referring now to FIG. 8, a step including depositing a gate dielectric 116 in the hollow dummy gates on the semiconductor device 10 is depicted according to an embodiment of the present invention.

According to aspects of the invention, a step is included for forming a dielectric layer in-between the first gate space 202 and the second gate spacers 302, and in-between the layers of second nanosheet material 114. This forms a dielectric layer around the interior of the space between each set of the first gate spacers 202 and the second gate spacers 302. The dielectric layer 116 may be formed concurrently in the first region 20 and the second region 30.

The dielectric layer 116 may be any suitable dielectric material, including but not limited to, silicon oxide, silicon nitride, silicon oxynitride, high-k materials, or any combination of these materials. Examples of high-k materials include but are not limited to metal oxides such as hafnium oxide, hafnium silicon oxide, hafnium silicon oxynitride, lanthanum oxide, lanthanum aluminum oxide, zirconium oxide, zirconium silicon oxide, zirconium silicon oxynitride, tantalum oxide, titanium oxide, barium strontium titanium oxide, barium titanium oxide, strontium titanium oxide, yttrium oxide, aluminum oxide, lead scandium tantalum oxide, and lead zinc niobate. The high-k may further include dopants such as lanthanum, aluminum, magnesium. The dielectric layer 116 may be formed as part of a deposition process, such as those discussed above.

Figure 9:
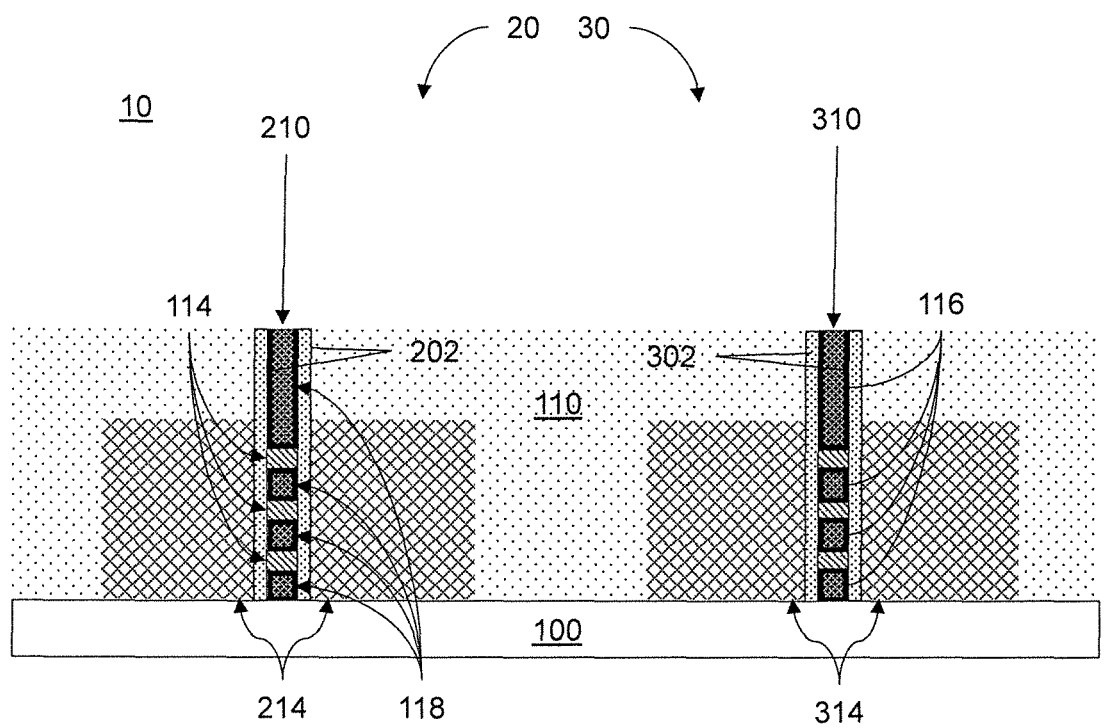
FIG. 9 is a cross-sectional view showing a gate metal formed within the dielectric layer of the semiconductor device of FIG. 9, in accordance with an embodiment of the present invention.

Referring now to FIG. 9, a step including forming a gate conductor 118 on the semiconductor device 10 is depicted according to an embodiment of the present invention.

According to aspects of the invention, a step for forming a gate conductor 118 in the first region 20 and the second region 30 is included. The gate conductor 118 is the same material in each of the first region 20 and the second region 30, and may be formed concurrently through a suitable deposition process, such as those discussed above. The gate conductor 118 is formed in-between the first gate spacers 202 and the second gate spacers 302, and between the second nanosheet material 114. As a result, a first stacked nanosheet gate 210 and a second stacked nanosheet gate 310 are formed on the substrate 100.

The material of the gate conductor 118 can be any suitable conducting material, including but not limited to, doped polycrystalline or amorphous silicon, germanium, silicon germanium, a metal (e.g., tungsten, titanium, tantalum, ruthenium, zirconium, cobalt, copper, aluminum, lead, platinum, tin, silver, gold), a conducting metallic compound material (e.g., tantalum nitride, titanium nitride, tantalum carbide, titanium carbide, titanium aluminum carbide, tungsten silicide, tungsten nitride, ruthenium oxide, cobalt silicide, nickel silicide), carbon nanotube, conductive carbon, graphene, or any suitable combination of these materials. The conductive material may further comprise dopants that are incorporated during or after deposition. In some embodiments, the gate conductor includes a workfunction metal layer to set the threshold voltage of the nanosheet transistor to a desired value. The work function layer may be a nitride, including but not limited to titanium nitride (TiN), titanium aluminum nitride (TiAlN), hafnium nitride (HfN), hafnium silicon nitride (HfSiN), tantalum nitride (TaN), tantalum silicon nitride (TaSiN), tungsten nitride (WN), molybdenum nitride (MoN), niobium nitride (NbN); a carbide, including but not limited to titanium carbide (TiC) titanium aluminum carbide (TiAlC), tantalum carbide (TaC), hafnium carbide (HfC), and combinations thereof.

Figure 10:
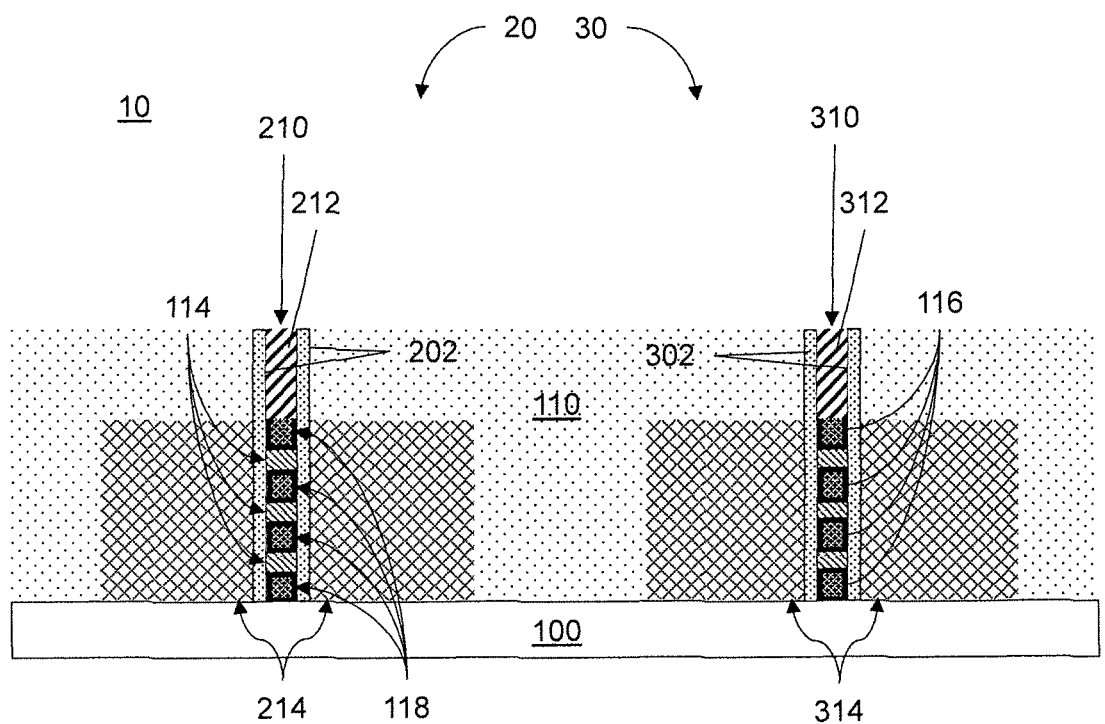
FIG. 10 is a cross-sectional view showing an insulating gate cap formed between the spacers of the semiconductor device of FIG. 10, in accordance with an embodiment of the present invention.

Referring now to FIG. 10, a step including forming a gate cap in each gate on the semiconductor device 10 is depicted according to an embodiment of the present invention.

With the first stacked nanosheet gate 210 and the second stacked nanosheet gate 310 formed, a step is included for forming a first gate cap 212 and a second gate cap 312. The first and second gate caps 212 and 312 are formed by recessing the metal in the first stacked nanosheet gate 210 and the second stacked nanosheet gate 310. An insulating material such as, e.g. an oxide or a nitride (for example, silicon nitride) is deposited within the recess of each of the first stacked nanosheet gate 210 and the second stacked nanosheet gate 310.

Figure 11:
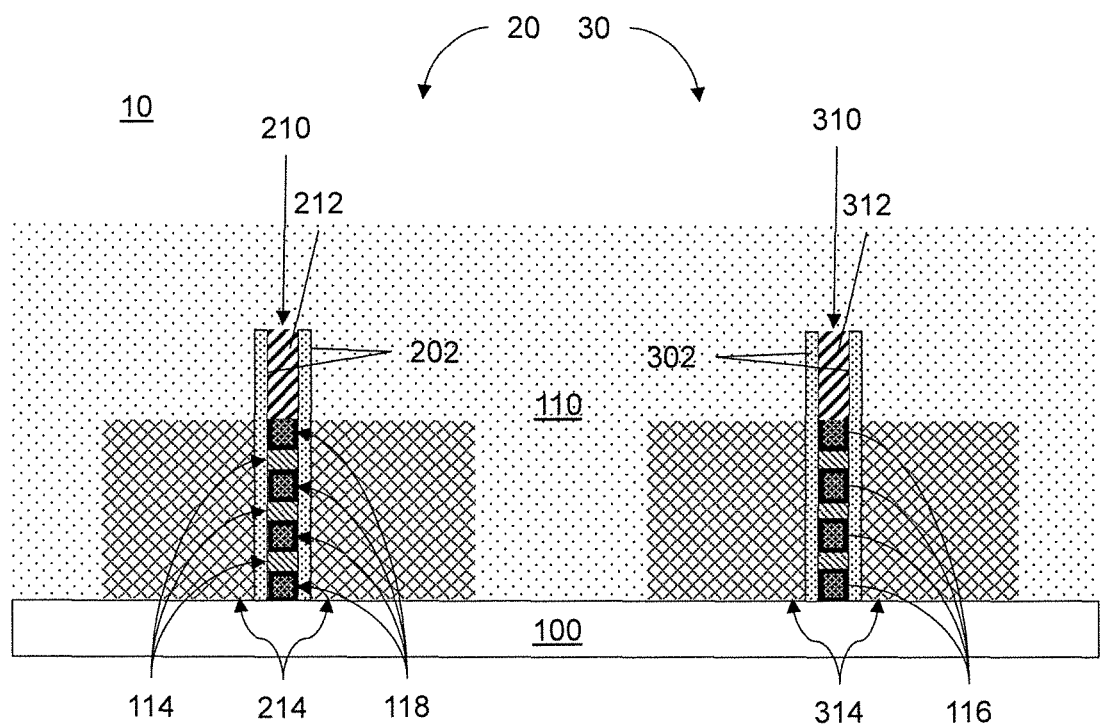
FIG. 11 is a cross-sectional view showing an additional layer of an interlevel dielectric layer formed over of the semiconductor device of FIG. 11, in accordance with an embodiment of the present invention.

Referring now to FIG. 11, a step including forming additional dielectric on the ILD 110 of the semiconductor device 10 is depicted according to an embodiment of the present invention.

A step may be included for depositing addition dielectric over the semiconductor device 10 to form a thicker ILD 110. The formation of the added dielectric may be performed according to similar processes as discussed above for forming ILD 110. Upon formation of the additional dielectric, the ILD 110 covers the first region 20 and the second region 30, including the first gate 210 and the second gate 310.

Figure 12:
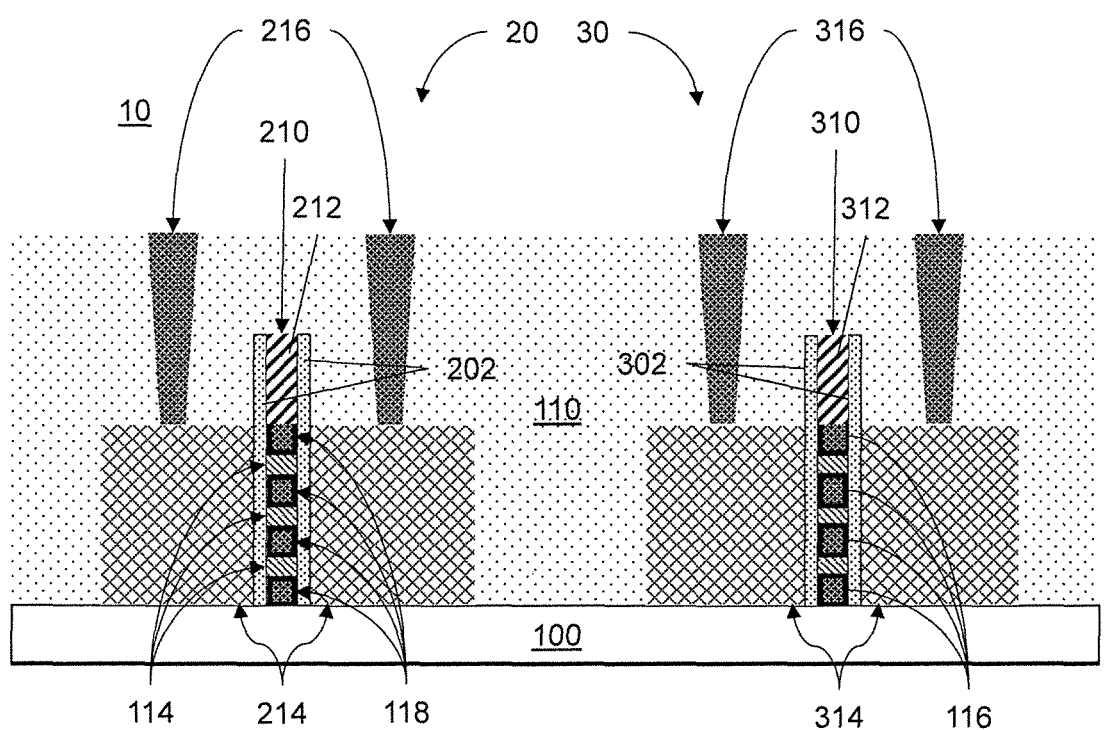
FIG. 12 is a cross-sectional view showing contacts formed through the interlevel dielectric layer of the semiconductor device of FIG. 12, in accordance with an embodiment of the present invention.
Figure 13:
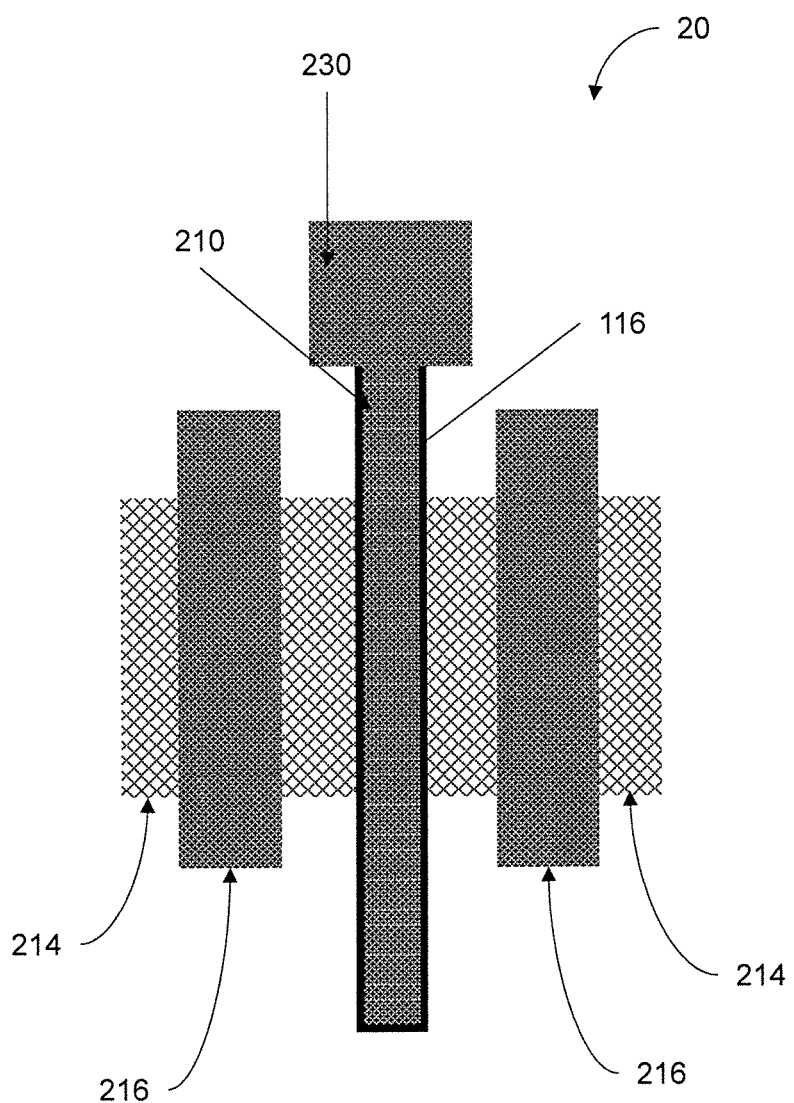
FIG. 13 is a top view showing a gate contact formed in one of the regions of the semiconductor device of FIG. 13, in accordance with an embodiment of the present invention.

Referring now to FIGS. 12-13, a step including forming contacts for the semiconductor device 10 is depicted according to an embodiment of the present invention.

Contacts may be formed on the semiconductor device 10. The contacts may include first source/drain contacts 216 in the first region 20, and second source/drain contacts 316 in the second region 30. Each of the first and the second source/drain contacts 216 and 316 may be formed concurrently by opening up the ILD 110 down to the first source/drain regions 214 and the second source drain region 314. A conducting material or a combination of conducting materials may then be deposited into the openings of the ILD 110 down to the source/drain contacts in each region. Thus, first source/drain contacts 216 and second source/drain contacts 316 are formed in both the first region 20 and the second region 30.

Accordingly, each of the first region 20 and the second region 30 includes a structure similar to a stacked nanosheet field effect transistor (FET). The structures in the first region 20 and the second region 30 may have each been formed concurrently by common processing steps. As a result, the first region 20 and the second region 30 are substantially structurally the same. Thus, the processing steps and processing time are reduced, resulting in a faster, more efficient process.

However, processing in each of the first region 20 and the second region 30 may differentiate at a step for forming a gate contact 230 in the first region 20, as depicted in FIG. 13.

The gate contact 230 may be formed concurrently with the first and second source/drain contacts 216 and 316, or it may be formed as a separate step. Nevertheless, the gate contact 230 is formed in the first region 20 and not in the second region 30, thus forming a functioning stacked nanosheet FET in the first region 20. The gate contact 230 may be formed from a metal such as the gate metal 118 and/or the metal used to form the first source/drain contacts 216.

Figure 14:
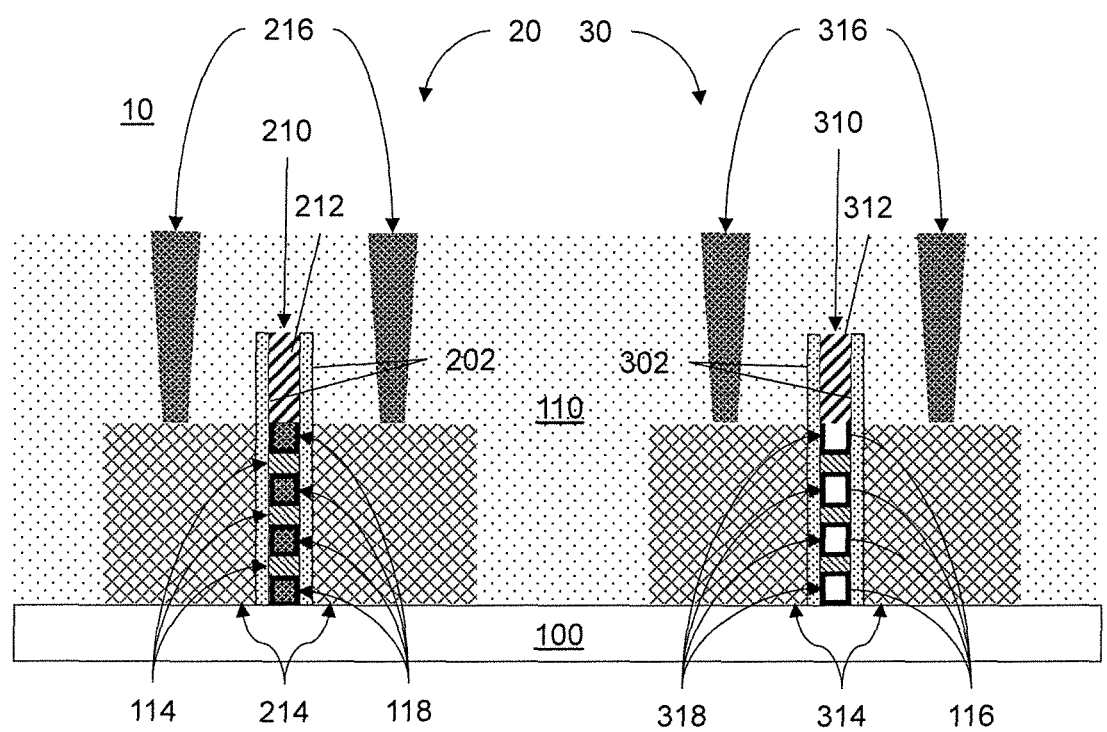
FIG. 14 is a cross-sectional view showing the gate metal removed from one of the regions of the semiconductor device of FIG. 13, in accordance with an embodiment of the present invention.
Figure 15:
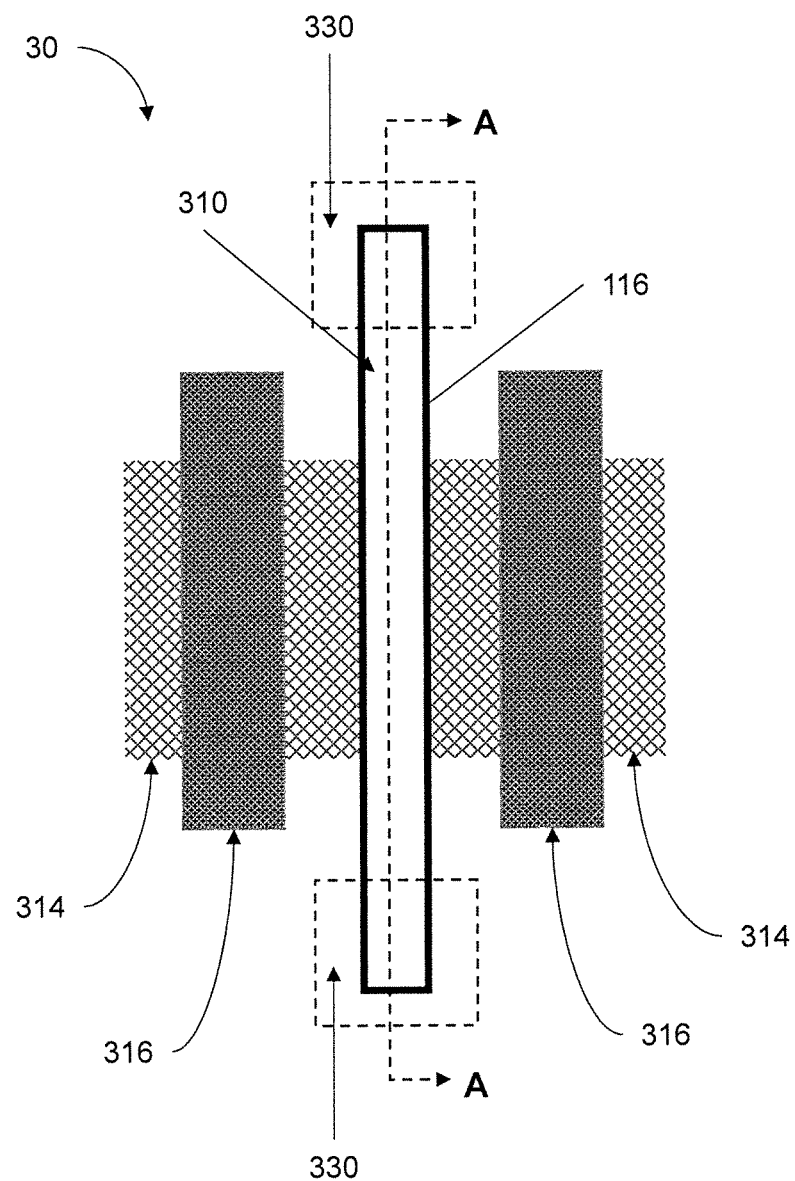
FIG. 15 is a top view showing reservoir openings in one regions of the semiconductor device of FIG. 15, in accordance with an embodiment of the present invention.
Figure 16:
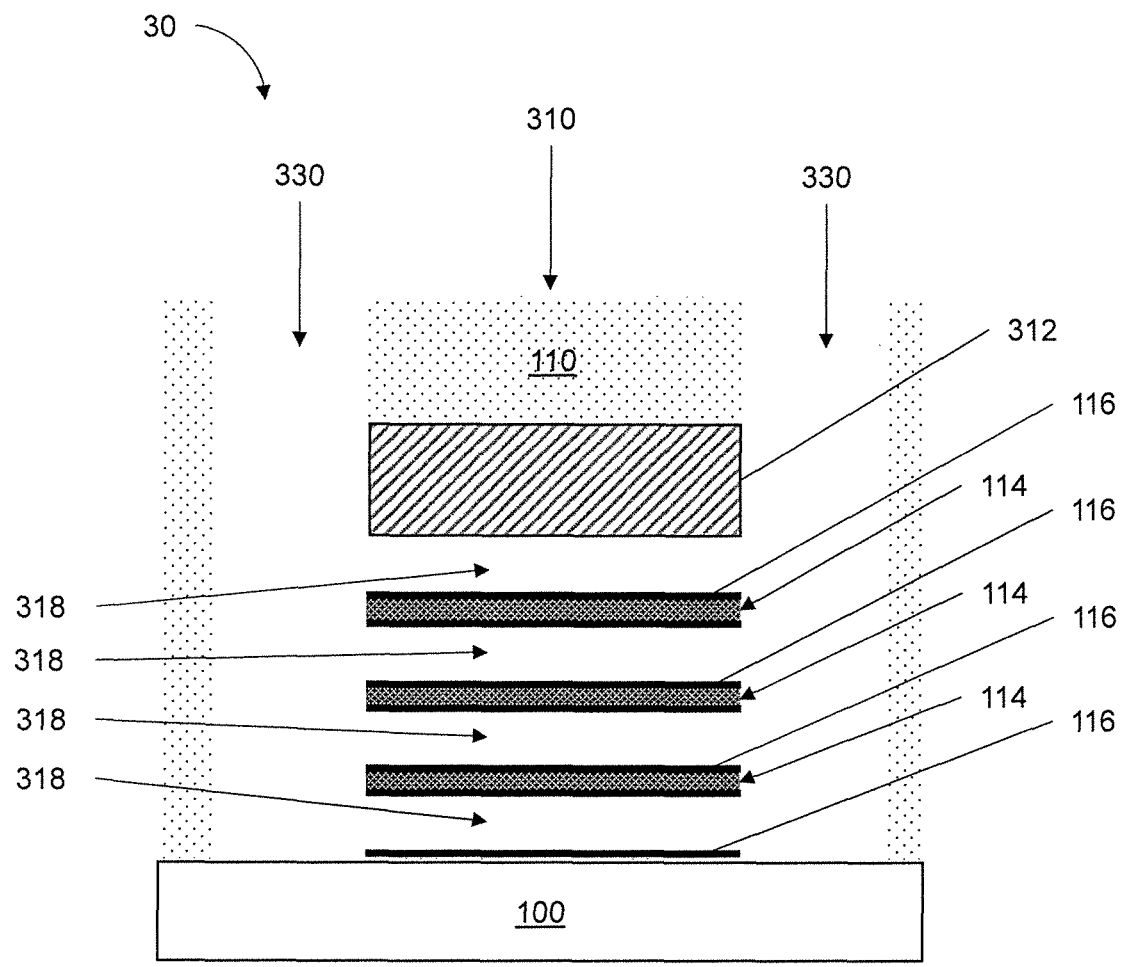
FIG. 16 is a cross-sectional view along line A of FIG. 16 showing a nanofluidic structure in one of the regions of the semiconductor device of FIG. 16 in accordance with an embodiment of the present invention.

Referring now to FIGS. 14-16, a step including forming channels in the second region 30 of the semiconductor device 10 is depicted according to an embodiment of the present invention.

A stacked nanofluidics sensor is formed in the second region 30 by including a step for opening reservoirs in the second region 30 and removing the gate metal 118 from the second region 30. To form the reservoirs 330, as depicted in FIG. 15, openings are created at each end of the second gate 310 in the second region 30. The reservoirs 330 have similar openings to an opening formed for the gate contact 230 in the second region 20, and thus may be opened using a similar processing step. Accordingly, the reservoirs 330 may be opened concurrently with the gate contact 230 opening using a common process, or the reservoirs 330 may be opened in a separate processing step. However, where the gate contact 230 is then filled with a deposited metal, the reservoirs 330 remain open. Therefore, the reservoirs 330 may accept and contain a fluid sample for analysis by the nanofluidic sensor while in operation.

According to one aspect of the invention, the reservoirs 330 are opened after the gate contact 230 by forming a mask over the first region 20 and opening the ILD 110 down to the substrate 100 at each end of the second stacked nanosheet gate 310. After opening the reservoirs 330, an etch process is performed to selectively remove the gate metal 118 from between the second gate spacers 302. As a result of the etch process, the second nanosheet material 114 and the dielectric layer 116 remain between the second gate spacers 302, thus forming channels 318 extending from one reservoir 330 to the other reservoir 330; as depicted in FIG. 16. Accordingly, a stacking nanofluidic sensor is formed in the second region 30, where, in operation, a fluid sample for analysis is accepted into one or both reservoirs 330 and flows through the channels 318. Electrical signals from the second source/drain regions 314 may then be used to analyze the fluid.

Because the channels 318 have been formed using a common process with a FET, the dimensions of the channels 318 are accurately and precisely determined. The length from one reservoir 330 to the other is determined according to the gate length as determined for a stack nanosheet transistor. Similarly, the width of the channels 318 are controlled by the gate width, as with a stacked nanosheet transistor. Finally, the height of each channel 318 is precisely controlled by the height of each layer of the sacrificial first nanosheet material 112 in the deposition process. Accordingly, the above process ensure that the dimensions of the channels 318 are precisely controlled.

When passing an electrical signal through a sample, the geometric dimensions of the sample effect the modulation of the electrical signal. Therefore, variability in the dimensions of the sample translates to variability in measurements of the electrical signal, thus decreasing accuracy. Because the channels 318 have precisely controlled geometric dimensions, as determined by factors such as gate length, gate width, and nanosheet height, measurements of electrical signals through the fluid sample in the channels can be more accurately made.

Moreover, because the formation of the channels 318 uses similar processes to forming the gate structure 210 of the first region 20, much of the structure in both the first region 20 and the second region 30 can be formed concurrently with common processing steps. Thus, the number of processing steps is reduced and a semiconductor device 10 including both a FET in the first region 20 and a nanofluidic sensor in the second region 30 can be produced more quickly and more efficiently.

Figure 17:
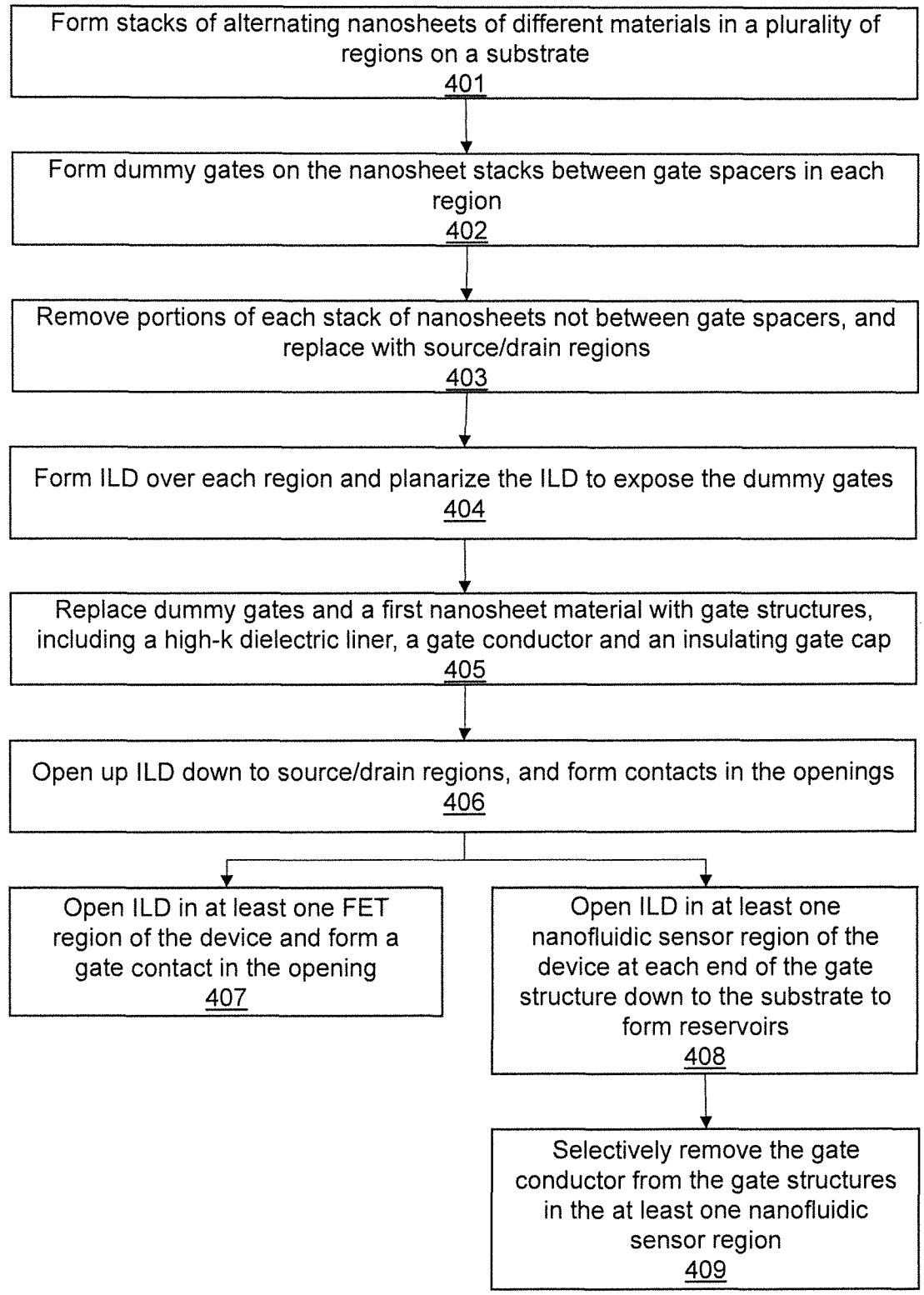
FIG. 17 is a block/flow diagram showing methods for forming stacked nanofluidic structures, in accordance with an embodiment of the present invention.

Referring now to FIG. 17, a method of forming the semiconductor device 10 is depicted according to an embodiment of the present invention.

According to aspects of the invention, a method for forming a stacked nanofluidic sensor on a semiconductor device is described. In the method, at block 401 stacks of alternating nanosheets of at least two different nanosheet materials are formed. The at least two different nanosheet materials are selectively etchable and each stack corresponds to a different region of the semiconductor device.

At block 402, dummy gates are formed on each stack of nanosheets in between gate spacers in each region.

At block 403, portions of each stack of nanosheets in each region that do not lie beneath or between the dummy gates are removed. The portions of the stacks may be removed by etching, planarizing or photolithography, using the dummy gates as a mask. Source/drain regions may then be deposited in areas previously occupied by the removed portions of the stacks, and abutting the dummy gates and remaining nanosheet materials.

At block 404, an ILD is formed over each region of the semiconductor device and planarized to expose the tops of the dummy gates. The ILD may be planarized by any suitable planarization process, such as CMP.

At block 405, a gate replacement process if performed to remove the dummy gates, as well as a first nanosheet material of the at least two different nanosheet materials from the dummy gates. Upon removal of the dummy gates and the first nanosheet material, a high-k dielectric liner is deposited, and filled with a gate conductor. The gate conductor may be any suitable conductive material, such as, e.g. a metal. The gate conductor is then recessed, and an insulating material is deposited to form a gate cap. The insulating material may be any suitable insulating material, such as an oxide or a nitride.

At block 406, the ILD is opened down to the source/drain regions in each region of the semiconductor device, and contacts are formed in the openings. The contacts may be formed from a suitable conductive material, such as, e.g., a metal. Thus source/drain contacts are formed.

At block 407, at least one of the regions of the semiconductor device is determined to be a FET region. In the at least one FET region, the ILD is opened down the substrate at an end of the gate structure. The opening is filled with a suitable conductive material, such as, e.g., a metal, to form a gate contact.

At block 408, at least one of the regions of the semiconductor device is determined to be a nanofluidic sensor region. In the at least one nanofluidic sensor region, the ILD is opened down to the substrate at both ends of the gate structure to form fluid reservoirs.

At block 409, the gate conductor of the gate structure in the at least one nanofluidic sensor region is selectively removed. Thus, openings in the gate structures between the remaining nanosheet material are formed, resulting in channels from one end of the gate structure to the other where the reservoirs are located. Accordingly, the nanofluidic sensor region includes channels in the gate structure enabling fluid communication from one reservoir to another.

Figure 18:
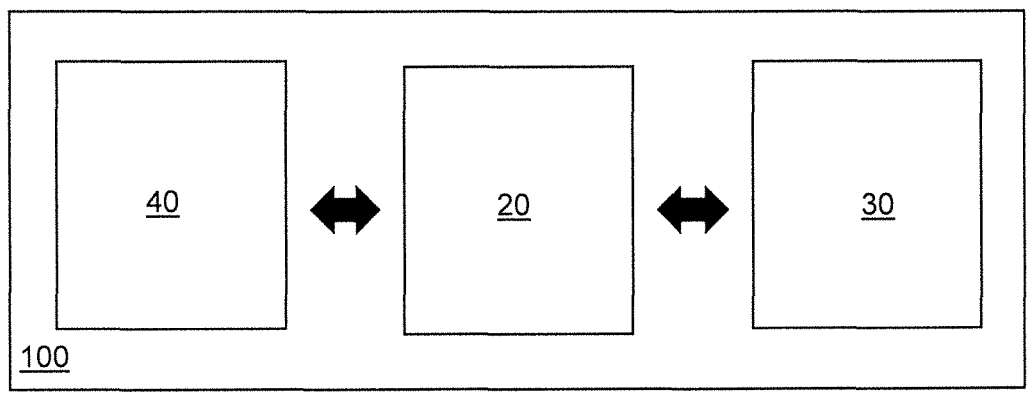
FIG. 18 is a block/flow diagram showing a system/method for using stacked nanofluidic structures, in accordance with an embodiment of the present invention.

Referring now to FIG. 18, depicting an exemplary semiconductor device 10 to which the present invention may be applied is shown in accordance with one embodiment.

The exemplary semiconductor device 10 may include a plurality of regions formed on a common substrate 100. The regions may include a nanofluidic sensor 30 and transistor regions 20 and 40. One transistor region may be a memory device 20, and the other may be a microprocessor 40.

A fluid sample may be input into one or both reservoirs of the nanofluidic sensor 30. The fluid may then communicate with the opposite reservoir by traveling through the channels of the nanofluidic sensor 30. Depending on the fluid and any particles suspended therein, the electrical properties of the fluid may change. Thus, an electrical current may be supplied to a source and transported through the gate structure to a drain. Since the gate metal has been removed from the gate structure to create the channels, the current signal will pass through the fluid sample as opposed to a gate metal. Accordingly, the electrical properties of the fluid sample within the channels will affect the current signal.

Transistors for a microprocessor 40, may detect the changes in the current signal from the nanofluidic sensor 30. The microprocessor 40 may then store data concerning the fluid sample in the transistor region for the memory 20. Similarly, the transistor region for the microprocessor 40 may read data in the memory 20 and control the nanofluidic sensor 30. Accordingly, each region of the semiconductor device may communicate, thus forming a complete lab-on-a-chip. Because the nanofluidic sensor 30 includes similar structures, including gate structures, to the transistors for memory 20 and the microprocessor 40, a large portion of the processing forming each region may be performed concurrently. As a result, the lab-on-a-chip is formed in a fast, efficient, and economical process.

Moreover, because the nanofluidic sensor utilizes a gate-like structure where channels are used instead of gate metal, the channels can be formed with the precision of forming a nanosheet transistor. As a result, the vertical height and lateral width of the channels are precisely controlled by the layer thickness and gate length, respectively, of fabricating a nanosheet transistor.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Reference in the specification to "one embodiment" or "an embodiment" of the present invention, as well as other variations thereof, means that a particular feature, structure, characteristic, and so forth described in connection with the embodiment is included in at least one embodiment of the present invention. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Having described preferred embodiments of a stacked nanofluidics structure and method of making a stacked nanofluidics structure (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A method for forming a stacked nanofluidic sensor, comprising:
   forming a nanosheet stack of at least two alternating layers of a first nanosheet material and a second nanosheet material on a substrate;
   forming a gate structure on the nanosheet stack; and
   forming nanofluidic channels within the gate structure by removing each layer of the first nanosheet material within the gate structure to form a channel configured to receive a nanofluidic sample.

2. The method of claim 1, further comprising:
   forming a source region and a drain region adjacent to the gate structure.

3. The method of claim 2, wherein forming the source region and the drain includes:
   etching portions of the nanosheet stack that are outside of a footprint of the gate structure; and
   replacing the etched portions with a conductive material abutting the gate structure.

4. The method of claim 1, further comprising forming an interlevel dielectric layer (ILD) around the nanosheet stack.

5. The method of claim 1, wherein forming the nanofluidic channels includes:
   recessing a dummy gate material from between gate spacers of the gate structure to expose the nanosheet stack;
   selectively etching the first nanosheet material to form cavities within the nanosheet stack between the second nanosheet material and the gate spacers;
   depositing a dielectric layer in the cavities;
   filling the cavities with the gate conductor;
   recessing a top of the gate conductor and deposit an insulating gate cap; and
   removing the gate conductor to form nanofluidic channels within a gate, wherein a fluid received in the nanofluidic channels acts as the gate conductor.

6. The method of claim 1, wherein the first nanosheet material include silicon germanium (SiGe) and the second nanosheet material includes silicon (Si).

7. The method of claim 1, further including forming reservoirs at each end of the gate structure.

8. The method of claim 7, forming the reservoirs includes opening an ILD down to the substrate at each end of the gate structure.

9. A method for forming a stacked nanofluidic sensor device, comprising:
   concurrently forming nanosheet stacks of at least two alternating layers of a first nanosheet material and a second nanosheet material in each of at least a first region and a second region on a substrate;
   concurrently forming a dummy gate over and around the nanosheet stack in each of at least the first region and the second region;
   concurrently forming gate structures in each of at least the first region and the second region by a gate replacement process, including replacing each layer of the first nanosheet material in each of at least the first region and the second region with a gate conductor;
   forming a transistor in the first region including the gate structure in the first region; and
   forming a nanofluidic sensor in the second region by removing the gate conductor from within the gate structure in the second region to form channels within the gate structure configured to receive a nanofluidic sample.

10. The method of claim 9, further comprising:
    forming a source region and a drain region adjacent to the dummy gate in each of the first region and the second region.

11. The method of claim 10, wherein forming the source region and the drain includes:
    etching portions of the nanosheet stack in each of the first region and the second region, wherein the etched portions are outside of a footprint of the dummy gate in each of the first region and the second region; and
    replacing the etched portions with a conductive material abutting the dummy gates.

12. The method of claim 9, further comprising forming an interlevel dielectric layer (ILD) over the first region and the second region.

13. The method of claim 9, wherein the gate replacement process includes forming a dielectric layer around the gate conductor material.

14. The method of claim 9, wherein the gate replacement process includes:
    recessing dummy gate material from between gate spacers to expose the nanosheet stack;

selectively etching the first nanosheet material to form cavities within the nanosheet stack between the second nanosheet material and the gate spacers;
depositing a dielectric layer in the cavities;
filling the cavities with the gate conductor; and
recessing a top of the gate conductor and depositing the insulating gate cap.

15. The method of claim 9, wherein the first nanosheet material include silicon germanium (SiGe) and the second nanosheet material includes silicon (Si).

16. The method of claim 9, further including:
opening an ILD down to the substrate at one end of the gate structure in the first region and depositing a gate contact in the opening; and
opening the ILD down to the substrate at each end of the gate structure in the second region to form reservoirs at each end of the gate structure in the second region.

* * * * *